United States Patent
Ohkuma et al.

(12) 
(10) Patent No.: US 6,794,471 B2
(45) Date of Patent: Sep. 21, 2004

(54) ACRYLIC ESTER COMPOUND USAGE THEREOF

(75) Inventors: Tadashi Ohkuma, Fukuoka (JP); Masao Imai, Chiba (JP); Mitsuo Nakamura, Chiba (JP); Atsuo Otsuji, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 254 days.

(21) Appl. No.: 09/960,308

(22) Filed: Sep. 24, 2001

(65) Prior Publication Data

US 2002/0061995 A1 May 23, 2002

(30) Foreign Application Priority Data

Sep. 22, 2000 (JP) .................................... 2000-288320

(51) Int. Cl.⁷ ..................... C08F 20/38; C07D 339/06
(52) U.S. Cl. ...................... 526/256; 526/286; 549/39
(58) Field of Search ................ 526/256, 286; 549/39

(56) References Cited

U.S. PATENT DOCUMENTS

| | | | |
|---|---|---|---|
| 5,670,657 A | * | 9/1997 | Kojima et al. ............... 549/39 |
| 6,307,062 B1 | * | 10/2001 | Caye et al. ................... 549/11 |

FOREIGN PATENT DOCUMENTS

| JP | 03-215801 A | 9/1991 |
|---|---|---|
| JP | 03-217412 A | 9/1991 |
| WO | WO 98-35955 A | 8/1998 |

* cited by examiner

Primary Examiner—Fred Teskin
(74) Attorney, Agent, or Firm—Burns, Doane, Swecker & Mathis, LLP

(57) ABSTRACT

An acrylic ester compound represented by the general formula (1):

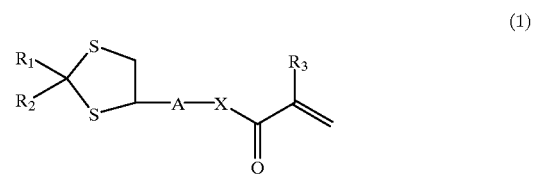

wherein, $R_1$ and $R_2$ represent independently a hydrogen atom, an alkyl group which may have a substituent, an aromatic alkyl group which may have a substituent or an aromatic residue which may have a substituent, respectively; $R_3$ represents a hydrogen atom or an alkyl group; A represents a divalent organic group; and X represents a sulfur atom or an oxygen atom; provided that when X is an oxygen atom, $R_1$ represents an aromatic residue that may have a substituent, a polymerizable composition comprising the compound, and a cured article and optical components obtained by polymerizing the polymerizable composition.

16 Claims, No Drawings

ACRYLIC ESTER COMPOUND USAGE THEREOF

BACKGROUND OF THE INVENTION

1. Field of the Invention

The present invention relates to an acrylic ester compound, a manufacturing method thereof and a sulfur-containing compound used as a synthetic intermediate thereof. Furthermore, the present invention relates to a polymerizable composition containing the acrylic ester compound, a cured article obtained by polymerizing the polymerizable composition and an optical component.

An acrylic ester compound of the present invention is a new compound that has a specific dithiolane ring system in the molecule and is useful as a monomer for photo-setting polymerizable compositions. Optical components that are obtained by curing the polymerizable composition have good optical property, thermal property, mechanical property, and outstanding productivity, and also have a high refractive index. It is also useful for various plastic lenses represented by a spectacles lens for correction, a base plate material for an optical information recording medium, a plastic base plate material for liquid crystal cells, an anti-reflection coating, a transparent coating material such as optical fiber coating material etc., an LED sealer and a dental material, etc.

2. Description of the Related Art

Since inorganic glass is excellent in transparency and in many physical properties and has a small optical anisotropy, it is widely used in the field of transparent optical materials. However, because it has such several problems that it is heavy, is easily damaged and is low in productivity, development of a resin for optical components (an organic optical material) that replaces inorganic glass is performed much in recent years.

Transparency is a fundamentally important characteristic as a resin for optical components. At present as industrial resins for optical components with sufficient transparency, poly methylmethacrylate (PMMA), bisphenol A polycarbonate (BPA-PC), polystyrene (PS), methylmethacrylate-styrene copolymer (MS), styrene-acrylonitrile copolymer (SAN), poly(4-methylpentene-1) (TPX), polycycloolefin (COP), poly(diethyleneglycol bisallyl carbonate) (EGAC), polythiourethane (PTU), etc. are known.

PMMA is excellent in transparency and weather resistance, and also in moldability. However, a refractive index (nd) is as small as 1.49, and there is a disadvantage of a high water absorbing property.

BPA-PC is excellent in transparency, heat resistance, impact resistance, and has a high refractive index, but a chromatic aberration is large and so a use field is limited.

Although excelled in moldability, transparency, a low water absorbing property, and high refractive index, PS and MS are inferior to impact resistance, weather resistance, and heat resistance, and therefore are hardly put in practical use as a resin for optical components.

The refractive index of SAN is comparatively high and mechanical property also has a good balance, but it has difficulty in heat resistance a little (heat deformation temperature: 80 to 90° C.), and is hardly used as a resin for optical components.

Although TPX and COP are excellent in transparency, low water absorbing property and heat resistance, they have a problem that impact resistance, gas barrier property, and dye ability are inferior, with a low refractive index (nd=1.47 to 1.53).

EGAC is a thermosetting resin that has diethyleneglycol bisallylcarbonate as a monomer, and is most used for a general-purpose spectacles lens. Although it is excellent in transparency and heat resistance, and a chromatic aberration is very small, it has a disadvantage of inferior impact resistance and a low refractive index (nd=1.50).

PTU is a thermosetting resin obtained by a reaction of diisocyanate compounds and polythiol compounds, and are most used for the super-high refractive index spectacles lens. Although it is a very excellent material because of especially superior transparency, impact resistance, high refractive index and small chromatic aberration, it has an only disadvantage that thermal polymerizing molding time is long (one to three days), and therefore has a problem in respect of productivity.

Several methods are proposed in order to raise the above described productivity and to perform polymerization and curing in a short time; a method of obtaining an optical lens by photo polymerization using an acrylic ester compound containing bromine atom or sulfur atom as a polymerizable compound (for example, Japanese Patent Laid-Open No. 63-248811, Japanese Patent Laid-Open No. 3-217412, etc.), a method of obtaining an optical lens using an (meth)acrylic ester compound which has a sulfur-containing aliphatic ring system (for example, Japanese Patent Laid-Open No. 3-215081 etc.).

However, according to these methods, the resin obtained was not accepted to be sufficient when used as optical materials. That is, it has such problems that, for example, working efficiency is decreased in the case of operation of being filtered or poured into a mold because of high viscosity of a polymerizable compound (monomer) and low fluidity, that although a polymerization can be performed in a short time a refractive index or Abbe number is not sufficiently high, that a lens with a high refractive index is brittle and fragile when used as a spectacles lens and that it has a high density. Therefore, development of materials has been strongly desired which may overcome these problems.

As mentioned above, although the conventional resins for optical components have outstanding characteristics, they have respective disadvantages to be overcome at present. Under such a circumstance, development of a resin for optical components is eagerly required that has a high refractive index, excellent workability and productivity, and also has an excellent transparency, thermal characteristics and mechanical properties.

SUMMARY OF THE INVENTION

An object of the present invention is to solve the disadvantages of the above-described conventional resins for optical components, and to provide a resin for optical components with a high refractive index, excellent workability and productivity, and at the same time with excellent transparency, thermal characteristics and mechanical properties.

The inventors reached the present invention as a result of having examined zealously in order to solve the above-described problems. That is, the present invention relates to an acrylic ester compound represented by the general formula (1):

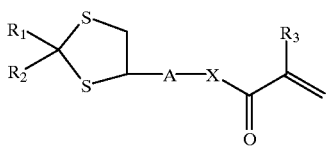

(1)

wherein, $R_1$ and $R_2$ represent independently a hydrogen atom, an alkyl group which may have a substituent, an aromatic alkyl group which may have a substituent or an aromatic residue which may have a substituent, respectively, $R_3$ represents a hydrogen atom or an alkyl group, A represents a divalent organic group and X represents a sulfur atom or an oxygen atom, provided that when X is an oxygen atom, $R_1$ represents an aromatic residue which may have a substituent.

Besides, the present invention relates to a polymerizable composition containing the acrylic ester compound represented by the above-described general formula (1), to a cured article obtained by polymerizing the polymerizable composition and further to optical components that comprise the cured article.

And also, the present invention relates to a method of manufacturing the acrylic ester compound represented by the above-described general formula (1), wherein a sulfur-containing compound represented by a following general formula (2) is esterified to form an acrylic ester. The present invention relates especially to the above described method characterized in that the above described compound represented by the general formula (2) is esterified to form an acrylic ester by dehydrohalogenation after the compound is reacted with halopropionic acids or halides thereof to form a halopropionic acid compound.

Furthermore, the present invention relates to a sulfur-containing compound represented by the general formula (2) useful as a raw material of the acrylic ester compound:

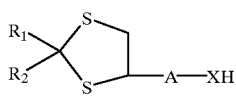

(2)

wherein $R_1$ and $R_2$ represent independently a hydrogen atom, an alkyl group which may have a substituent, an aromatic alkyl group which may have a substituent or an aromatic residue which may have a substituent, respectively, A represents a divalent organic group and X represents a sulfur atom or an oxygen atom, provided that when X is an oxygen atom, $R_1$ represents an aromatic residue that may have a substituent.

The acrylic ester compound of the present invention is very useful in uses, such as optical materials and dental materials, as a monomer for optical curable polymerizable compositions. The optical components obtained by curing the polymerizable composition can be polymerized, cured and molded in a short time (high productivity), and has good thermal characteristics and mechanical properties and a high refractive index. The optical components are useful for various plastic lenses represented by a spectacles lens for correction, a base plate material for an optical information recording medium, a plastics base plate material for liquid crystal cells, a coating material for optical fiber, etc.

Besides, it became possible by the present invention to provide the sulfur-containing compound represented by the general formula (2) that is very useful as a raw material of the above described acrylic ester compound.

DETAILED DESCRIPTION OF THE PREFERRED EMBODIMENTS

Hereinafter, the present invention will be described in detail.

The acrylic ester compound represented by the general formula (1) of the present invention is a novel compound characterized by having a specific dithiolane ring system in the structure.

In the general formula (1), $R_1$ and $R_2$ represent independently a hydrogen atom, an alkyl group that may have a substituent, an aromatic alkyl group that may have a substituent or an aromatic residue that may have a substituent, respectively. Here, for an "aromatic alkyl group" and an "aromatic residue", a bond with aromatic ring is formed via an alkyl group in the former case, and a bond is directly formed with a constitutional atom of an aromatic ring in the latter case. That is, this means that the aromatic ring in these groups may be a heterocyclic ring that has an aromaticity and contains a heteroatom.

However, when X in the general formula (1) is an oxygen atom, $R_1$ represents an aromatic residue that may have a substituent.

When $R_1$ or/and $R_2$ are an alkyl groups which may have a substituent, as the substituent contained in this alkyl group, alkoxy group, alkoxyalkoxy group, aralkyloxy group, aryloxy group, aryloxyalkoxy group, alkylthio group, alkylthioalkylthio group, aralkylthio group, arylthio group or arylthioalkylthio group may be mentioned.

When $R_1$ or/and $R_2$ are aromatic alkyl groups or aromatic residues that may have a substituent, the aromatic ring in the aromatic alkyl groups or the aromatic residues are preferably substituted. As the substituent, alkyl group, alkoxy group, alkoxyalkoxy group, aralkyloxy group, aryl group, aryloxy group, aryloxyalkyloxy group, alkylthio group, alkylthioalkylthio group, aralkylthio group, arylthio group, arylthioalkylthio group or a halogen atom may be mentioned.

As aromatic rings in an aromatic alkyl group or an aromatic residue in which $R_1$ or/and $R_2$ may have a substituent, aromatic hydrocarbons, such as benzene, naphthalene, anthracene and phenanthrene, or rings, such as heterocyclic rings which have an aromaticity as thiophene, pyridine, pyrrole, furan, γ-pyrane, γ-thiopyrane, thiazole, imidazole, pyrimidine, 1,3,5-triazine, indole, quinoline, purine, etc., may be mentioned.

It is preferable that the substituent $R_1$ and $R_2$ in the general formula (1) is independently a hydrogen atom, an alkyl group that may have a linear or a cyclic alkyl group with 1 to 20 carbon atoms which may have a substituent or the combination of the linear and the cyclic alkyl groups, an aromatic alkyl group with 5 to 20 carbon atoms which may have a substituent or an aromatic residue with 4 to 20 carbon atoms which may have a substituent respectively. And it is more preferable that the substituent $R_1$ and $R_2$ is a hydrogen atom, an alkyl group that may have a linear or a cyclic alkyl group with 1 to 8 carbon atoms which may have a substituent or the combination of the linear and the cyclic alkyl groups, an aromatic alkyl group with 5 to 12 carbon atoms which may have a substituent or an aromatic residue with 4 to 12 carbon atoms which may have a substituent.

As examples of the substituent $R_1$ and $R_2$;

hydrogen atom, a linear, branched, or cyclic alkyl group such as methyl group, ethyl group, n-propyl group, isopropyl group, n-butyl group, isobutyl group, tert-butyl group, n-pentyl group, isopentyl group, n-hexyl group, heptyl group, octyl group, cyclohexyl group and cyclohexyl methyl group, substituted or unsubstituted aromatic alkyl group such as benzyl group, 4-methylbenzyl group, 4-chlorobenzyl group, 4-bromobenzyl group and β-phenyl ethyl group, a substituted or unsubstituted aromatic residue such as phenyl group, 4-methylphenyl group, 3-methylphenyl group, 2-methylphenyl group, 4-methoxyphenyl group, 3-methoxyphenyl group, 2-methoxyphenyl group, 4-phenylphenyl group, 4-phenoxyphenyl group, 3-phenoxyphenyl group, 2-phenoxyphenyl group, 4-methylthiophenyl group, 3-methylthiophenyl group, 2-methylthiophenyl group, 4-chlorophenyl group, 3-chlorophenyl group, 2-chlorophenyl group, 4-bromophenyl group, 3-bromophenyl group, 2-bromophenyl group, α-naphthyl group, β-naphthyl group, 2-furyl group, 3-furyl group, a thiophen-2-yl group, a thiophen-3-yl group may be mentioned.

As the substituent $R_1$ and/or $R_2$, hydrogen atom, methyl group, benzyl group, β-phenyl ethyl group, phenyl group, thiophen-2-yl group, thiophen-3-yl group, 4-phenylphenyl group, α-naphthyl group or β-naphthyl group is still more preferable.

When an effect of the present invention is taken into consideration, phenyl group, thiophen-2-yl group, thiophen-3-yl group, 4-phenylphenyl group, α-naphthyl group or β-naphthyl group is especially preferable as the substituent $R_1$.

In the general formula (1), $R_3$ represents a hydrogen atom or an alkyl group.

The substituent $R_3$ is preferably a hydrogen atom or an alkyl group with 1 to 4 carbon atoms and more preferably a hydrogen atom or a methyl group.

In the general formula (1), A represents a divalent organic group.

The organic group A is preferably an alkylene group which may contain oxygen atom or sulfur atom, more preferably an alkylene group with 1 to 10 carbon atoms which may contain oxygen atom or sulfur atom and still more preferably a group represented by the following formula (a):

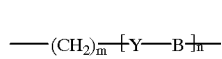

(a)

In the above formula (a), B represents an alkylene group with one to three carbon atoms, and preferably represents a methylene group, a 1,2-ethylene group, a trimethylene group or propylene group (1-methyl-1,2-ethylene group).

In the above formula (a), Y is an oxygen atom or a sulfur atom, and preferably is a sulfur atom.

In the above formula (a), m is an integer of 1 to 3, and preferably an integer of 1 to 2 and still preferably 1.

In the above formula (a), preferably, n is an integer of 0 to 3, and preferably an integer of 0 to 2, still preferably 0 or 1 and still more preferably 0.

In the general formula (1), X represents an oxygen atom or a sulfur atom, and preferably a sulfur atom.

In order to acquire various desired effects of the present invention, in the general formula (1), either $R_1$ or $R_2$ is preferably an aromatic residue which may have a substituent, and more preferably X is a sulfur atom and $R_1$ is an aromatic residue which may have a substituent and $R_2$ is a hydrogen atom.

As the acrylic ester compound represented by the general formula (1) of the present invention, for example;

4-acryloylthiomethyl-1,3-dithiolane,
2-methyl-4-acryloylthiomethyl-1,3-dithiolane,
2-ethyl-4-acryloylthiomethyl-1,3-dithiolane,
2-n-propyl-4-acryloylthiomethyl-1,3-dithiolane,
2-n-butyl-4-acryloylthiomethyl-1,3-dithiolane,
2-phenyl-4-acryloylthiomethyl-1,3-dithiolane,
2-(4'-methylphenyl)-4-acryloylthiomethyl-1,3-dithiolane,
2-(3'-methylphenyl)-4-acryloylthiomethyl-1,3-dithiolane,
2-(2'-methylphenyl)-4-acryloylthiomethyl-1,3-dithiolane,
2-(4'-tert-butylphenyl)-4-acryloylthiomethyl-1,3-dithiolane,
2-(4'-methoxyphenyl)-4-acryloylthiomethyl-1,3-dithiolane,
2-(4-phenylphenyl)-4-acryloylthiomethyl-1,3-dithiolane,
2-(4'-phenoxyphenyl)-4-acryloylthiomethyl-1,3-dithiolane,
2-(4'-methylthiophenyl)-4-acryloylthiomethyl-1,3-dithiolane,
2-(2,4,6-trimethylthiophenyl)-4-acryloylthiomethyl-1,3-dithiolane,
2-(4'-chlorophenyl)-4-acryloylthiomethyl-1,3-dithiolane,
2-(4'-bromophenyl)-4-acryloylthiomethyl-1,3-dithiolane,
2-(α-naphthyl)-4-acryloylthiomethyl-1,3-dithiolane,
2-(β-naphthyl)-4-acryloylthiomethyl-1,3-dithiolane,
2,2-dimethyl-4-acryloylthiomethyl-1,3-dithiolane,
2-methyl-2-phenyl-4-acryloylthiomethyl-1,3-dithiolane,
2,2-diphenyl-4-acryloylthiomethyl-1,3-dithiolane,
4-(2-acryloylthioethyl)-1,3-dithiolane,
4-(3-acryloylthiopropyl)-1,3-dithiolane,
4-(2-methyl-2-acryloylthioethyl)-1,3-dithiolane,
4-acryloylthiomethylthiomethyl-1,3-dithiolane,
4-(2-acryloylthioethylthio)methyl-1,3-dithiolane,
4-(3-acryloylthiopropylthio)methyl-1,3-dithiolane,
4-(2-methyl-2-acryloylthioethylthio)methyl-1,3-dithiolane,
4-[2-(acryloylthiomethylthio)ethyl]-1,3-dithiolane,
4-[2-(2-acryloylthioethylthio)ethyl]-1,3-dithiolane,
4-[2-(3-acryloylthiopropylthio) ethyl]-1,3-dithiolane,
4-[2-(2-methyl-2-acryloylthioethylthio) ethyl]-1,3-dithiolane,
4-[3-(acryloylthiomethylthio)propyl]-1,3-dithiolane,
4-[3-(2-acryloylthioethylthio) propyl]-1,3-dithiolane,
4-[3-(3-acryloylthiopropylthio)propyl]-1,3-dithiolane,
4-[3-(2-methyl-2-acryloylthioethylthio)propyl]-1,3-dithiolane,
4-[2-methyl-2-(acryloylthiomethylthio)ethyl]-1,3-dithiolane,
4-[2-methyl-2-(2-acryloylthioethylthio)ethyl]-1,3-dithiolane,
4-[2-methyl-2-(3-acryloylthiopropylthio)ethyl]-1,3-dithiolane,
4-[2-methyl-2-(2-methyl-2-acryloylthioethylthio)ethyl]-1,3-dithiolane,
2-(4-methylphenyl)-4-(2-acryloylthioethyl)-1,3-dithiolane,
2-α-naphthyl-4-(3-acryloylthiopropyl)-1,3-dithiolane,
2-phenyl-4-(acryloylthiomethylthio)methyl-1,3-dithiolane,
2-(4-methoxyphenyl)-4-(2-acryloylthioethylthio)methyl-1,3-dithiolane,
2-(4-bromophenyl)-4-(2-acryloylthiopropylthio)methyl-1,3-dithiolane,
2-(thiophen-2-yl)-4-(2-methyl-2-acryloylthioethylthio)methyl-1,3-dithiolane,
2-furyl-4-[2-(2-acryloylthioethylthio)ethyl]-1,3-dithiolane,
2-(4-methylthiophenyl)-4-[3-(acryloylthiomethylthio)propyl]-1,3-dithiolane,
2-β-naphthyl-4-[2-methyl-2-(acryloylthiomethylthio)ethyl]-1,3-dithiolane,
2-methyl-4-acryloyloxymethyl-1,3-dithiolane, 2-phenyl-4-acryloyloxymethyl-1,3-dithiolane,
2-(4'-methylphenyl)-4-acryloyloxymethyl-1,3-dithiolane,
2-(4'-methoxyphenyl)-4-acryloyloxymethyl-1,3-dithiolane,
2-(4-phenylphenyl)-4-acryloyloxymethyl-1,3-dithiolane,
2-(4'-phenoxyphenyl)-4-acryloyloxymethyl-1,3-dithiolane,
2-(4'-methylthiophenyl)-4-acryloyloxymethyl-1,3-dithiolane,
2-(2,4,6-trimethylthiophenyl)-4-acryloyloxymethyl-1,3-dithiolane,
2-(4'-chlorophenyl)-4-acryloyloxymethyl-1,3-dithiolane,
2-(4'-bromophenyl)-4-acryloyloxymethyl-1,3-dithiolane,
2-(α-naphthyl)-4-acryloyloxymethyl-1,3-dithiolane,
2-(β-naphthyl)-4-acryloyloxymethyl-1,3-dithiolane,
2-methyl-2-phenyl-4-acryloyloxymethyl-1,3-dithiolane,
2,2-diphenyl-4-acryloyloxymethyl-1,3-dithiolane,
2-(4-methylphenyl)-4-(2-acryloyloxyethyl)-1,3-dithiolane,
2-α-naphthyl-4-(3-acryloyloxypropyl)-1,3-dithiolane,
2-phenyl-4-(acryloyloxymethylthio)methyl-1,3-dithiolane,
2-(4-methoxyphenyl)-4-(2-acryloyloxyethylthio)methyl-1,3-dithiolane,
2-(4-bromophenyl)-4-(2-acryloyloxypropylthio)methyl-1,3-dithiolane,
2-(thiophen-2-yl)-4-(2-methyl-2-acryloyloxyethylthio)methyl-1,3-dithiolane,
2-furyl-4-[2-(2-acryloyloxyethylthio)ethyl]-1,3-dithiolane,
2-(4'-methylthiophenyl)-4-[3-(acryloyloxymethylthio)propyl]-1,3-dithiolane,
2-β-naphthyl-4-[2-methyl-2-(acryloyloxymethylthio)ethyl]-1,3-dithiolane,
4-methacryloylthiomethyl-1,3-dithiolane,
2-methyl-4-methacryloylthiomethyl-1,3-dithiolane,
2-ethyl-4-methacryloylthiomethyl-1,3-dithiolane,
2-n-propyl-4-methacryloylthiomethyl-1,3-dithiolane,
2-n-butyl-4-methacryloylthiomethyl-1,3-dithiolane,
2-phenyl-4-methacryloylthiomethyl-1,3-dithiolane,
2-(4'-methylphenyl)-4-methacryloylthiomethyl-1,3-dithiolane,
2-(3'-methylphenyl)-4-methacryloylthiomethyl-1,3-dithiolane,
2-(2'-methylphenyl)-4-methacryloylthiomethyl-1,3-dithiolane,
2-(4'-tert-butylphenyl)-4-methacryloylthiomethyl-1,3-dithiolane,
2-(4'-methoxyphenyl)-4-methacryloylthiomethyl-1,3-dithiolane,
2-(4'-phenylphenyl)-4-methacryloylthiomethyl-1,3-dithiolane,
2-(4'-phenoxyphenyl)-4-methacryloylthiomethyl-1,3-dithiolane,
2-(4'-methylthiophenyl)-4-methacryloylthiomethyl-1,3-dithiolane,
2-(2,4,6-trimethylthiophenyl)-4-methacryloylthiomethyl-1,3-dithiolane,
2-(4'-chlorophenyl)-4-methacryloylthiomethyl-1,3-dithiolane,
2-(4'-bromophenyl)-4-methacryloylthiomethyl-1,3-dithiolane,
2-(α-naphthyl)-4-methacryloylthiomethyl-1,3-dithiolane,
2-(β-naphthyl)-4-methacryloylthiomethyl-1,3-dithiolane,
2,2-dimethyl-4-methacryloylthiomethyl-1,3-dithiolane,
2-methyl-2-phenyl-4-methacryloylthiomethyl-1,3-dithiolane,
2,2-diphenyl-4-methacryloylthiomethyl-1,3-dithiolane,
4-(2-methacryloylthioethyl)-1,3-dithiolane,
4-(3-methacryloylthiopropyl)-1,3-dithiolane,
4-(2-methyl-2-methacryloylthioethyl)-1,3-dithiolane,
4-methacryloylthiomethylthiomethyl-1,3-dithiolane,
4-(2-methacrylythioethylthio)methyl-1,3-dithiolane,
4-(3-methacryloylthiopropylthio)methyl-1,3-dithiolane,
4-(2-methyl-2-methacryloylthioethylthio)methyl-1,3-dithiolane,
4-[2-(methacryloylthiomethylthio)ethyl]-1,3-dithiolane,
4-[2-(2-methacryloylthioethylthio)ethyl]-1,3-dithiolane,
4-[2-(3-methacryloylthiopropylthio)ethyl]-1,3-dithiolane,
4-[2-(2-methyl-2-methacryloylthioethylthio)ethyl]-1,3-dithiolane,
4-[3-(methacryloylthiomethylthio)propyl]-1,3-dithiolane,
4-[3-(2-methacryloylthioethylthio)propyl]-1,3-dithiolane,
4-[3-(3-methacryloylthiopropylthio)propyl]-1,3-dithiolane,
4-[3-(2-methyl-2-methacryloylthioethylthio)propyl]-1,3-dithiolane,
4-[2-methyl-2-(methacryloylthiomethylthio)ethyl]-1,3-dithiolane,
4-[2-methyl-2-(2-methacryloylthioethylthio)ethyl]-1,3-dithiolane,
4-[2-methyl-2-(3-methacryloylthiopropylthio)ethyl]-1,3-dithiolane,
4-[2-methyl-2-(2-methyl-2-methacryloylthioethylthio)ethyl]-1,3-dithiolane,
2-(4-methylphenyl)-4-(2-methacryloylthioethyl)-1,3-dithiolane,
2-α-naphthyl-4-(3-methacryloylthiopropyl)-1,3-dithiolane,
2-phenyl-4-(methacryloylthiomethylthio)methyl-1,3-dithiolane,
2-(4-methoxyphenyl)-4-(2-methacryloylthioethylthio)methyl-1,3-dithiolane,
2-(4-bromophenyl)-4-(2-methacryloylthiopropylthio)methyl-1,3-dithiolane,
2-(thiophen-2-yl)-4-(2-methyl-2-methacryloylthioethylthio)methyl-1,3-dithiolane,
2-furyl-4-[2-(2-methacryloylthioethylthio)ethyl]-1,3-dithiolane,
2-(4-methylthiophenyl)-4-[3-(methacryloylthiomethylthio)propyl]-1,3-dithiolane,
2-β-naphthyl-4-[2-methyl-2-(methacryloylthiomethylthio)ethyl]-1,3-dithiolane,
2-methyl-4-methacryloyloxymethyl-1,3-dithiolane,
2-phenyl-4-methacrylyoxymethyl-1,3-dithiolane,
2-(4'-methylphenyl)-4-methacryloyloxymethyl-1,3-dithiolane,
2-(4'-methoxyphenyl)-4-methacryloyloxymethyl-1,3-dithiolane,
2-(4'-phenylphenyl)-4-methacryloyloxymethyl-1,3-dithiolane,
2-(4'-phenoxyphenyl)-4-methacryloyloxymethyl-1,3-dithiolane,
2-(4'-methylthiophenyl)-4-methacryloyloxymethyl-1,3-dithiolane,
2-(2,4,6-trimehylthiophenyl)-4-methacryloyloxymethyl-1,3-dithiolane,
2-(4-chlorophenyl)-4-methacryloyloxymethyl-1,3-dithiolane,
2-(4'-bromophenyl)-4-methacryloyloxymethyl-1,3-dithiolane,
2-(α-naphthyl)-4-methacryloyloxymethyl-1,3-dithiolane,
2-(β-naphthyl)-4-methacryloyloxymethyl-1,3-dithiolane,
2-methyl-2-phenyl-4-methacryloyloxymethyl-1,3-dithiolane,
2,2-diphenyl-4-methacryloyloxymethyl-1,3-dithiolane,
2-(4-methyl phenyl)-4-(2-methacryloyloxyethyl)-1,3-dithiolane,
2-α-naphthyl-4-(3-methacryloyloxypropyl)-1,3-dithiolane,
2-phenyl-4-(methacryloyloxymethylthio)methyl-1,3-dithiolane, 2-(4-methoxyphenyl)-4-(2-methacryloyloxyethylthio)
methyl-1,3-dithiolane,
2-(4-bromophenyl)-4-(2-methacryloyloxypropylthio)
methyl-1,3-dithiolane,
2-(thiophen-2-yl)-4-(2-methyl-2-methacryloyloxyethylthio)
methyl-1,3-dithiolane,
2-furyl-4-[2-(2-methacryloyloxyethylthio)ethyl]-1,3-
dithiolane,
2-(4-methylthiophenyl)-4-[3-(methacryloyloxymethylthio)
propyl]-1,3-dithiolane,
2-β-naphthyl-4-[2-methyl-2-(methacryloyloxymethylthio)
ethyl]-1,3-dithiolane, etc. may be mentioned but the
present invention is not limited by them.

The acrylic ester compound represented by the general
formula (1) of the present invention is preferably manufactured by various kinds of esterifying methods in which the
reaction itself is well-known by using as a raw material the
sulfur-containing compound represented by the general formula (2). That is, the acrylic ester compound represented by
the general formula (1) is manufactured by applying to the
sulfur-containing compound represented by the following
general formula (2) various well-known esterification methods shown by the following typical example method:

(1) A method in which (meth)acrylic acid (for example,
(meth)acrylic acid, its acid halide, or its ester derivative
etc.) is reacted to obtain (meth)acrylic ester, (for
example, methods given in Japanese Patent Laid-Open
Nos. 64-26613, 64-31759 and 63-188660, etc.);

(2) A method in which acrylic ester is obtained by being
dehalogenated after halopropionic acids (for example,
3-chloropropionic acid, 3-bromopropionic acid,
3-chloro-2-methylpropionic acid, 3-bromo-2-
methylpropionic acid, etc.) or its halides is reacted, to
obtain halopropionic acid ester, (for example, methods
given in Japanese Patent Laid-Open Nos. 10-204056,
2-172968, 2-172969 and 4-29967, etc.).

Formula (2) being:

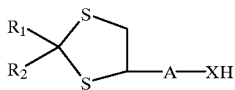

(2)

wherein $R_1$, $R_2$, and A and X are the same as the above.

In the above described methods, the method of above
described latter (2) is more preferable as a method of
manufacturing the acrylic ester compound represented by
the general formula (1) of the present invention.

Also in this method, a method shown in the following
reaction scheme is still more preferable; namely, a method
of manufacturing the acrylic ester compound represented by
the general formula (1) in which, after obtaining a halopropionic acid ester compound (3) by reacting the sulfur-containing compound represented by the above described
general formula (2) with the acid halide of halopropionic
acid, a dehydrohalogenation of this halopropionic acid ester
compound (3) is performed in the presence of a base.

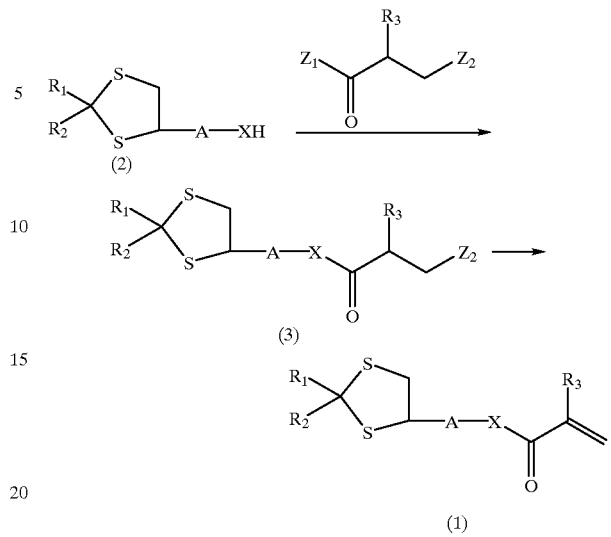

wherein, $R_1$, $R_2$, $R_3$, and A and X are the same as the above,
and $Z_1$ and $Z_2$ independently represent a chlorine atom or a
bromine atom.

Hereinafter, the method will be described in more detail.
First, a reaction of the sulfur-containing compound represented by the general formula (2) with an acid halide of
halopropionic acids to obtain the halopropionic acid ester
compound (3) will be described in detail.

Although In the case of this reaction the amount of acid
halide of the halopropionic acids used (for example,
3-chloropropionic acid, 3-bromopropionic acid, 3-chloro-2-
methylpropionic acid, 3-bromo-2-methylpropionic acid,
etc.) that is reacted to the sulfur-containing compound
represented by the general formula (2) is not especially
limited, usually, it is 0.1 to 5 moles, and preferably 0.2 to 3
moles and more preferably 0.5 to 2 moles to one mole of the
sulfur-containing compounds. The amount of the acid halide
of halopropionic acids used is especially preferably 0.8 to
1.5 moles.

The reaction may be performed without solvent or may be
performed in a solvent that is inactive to the reaction. The
solvent used is not limited in particular if it is an inactive
solvent. The reaction may be performed in, for example,
water or any organic solvents or a mixture thereof. As the
organic solvent, hydrocarbon solvents such as n-hexane,
benzene and toluene, ketone solvents such as acetone,
methylethyl ketone, and methyl isobutyl ketone, ester solvents such as ethyl acetate and butyl acetate, ether solvents
such as diethyl ether, diethyleneglycol dimethylether, tetrahydrofuran and dioxane, halogen solvents such as
dichloromethane, chloroform, carbontetrachloride, 1,2-
dichloroethane, tetrachloroethylene, chlorobenzene and
ortho-chlorobenzene, polar solvents such as acetonitrile,
N,N-dimethylformamide, N,N-dimethyl imidazolidinone,
dimethyl sulfoxide and sulfolane may be mentioned. These
solvents may be used singly or in combination of two or
more thereof.

In particular, the reaction temperature is not limited, but
is usually −78 to 150° C., preferably −20 to 120° C., and
more preferably 0 to 100° C.

The reaction time is dependent on the reaction
temperature, and, usually it is several minutes to 100 hours,
preferably 30 minutes to 50 hours and more preferably one
to 20 hours. Besides, while the rate of a reaction is checked
by well-known analytical means (for example, liquid chromatography, gas chromatography, thin layer chromatography, IR, etc.), the reaction may be stopped at an arbitrary rate of the reaction.

This reaction may be performed without catalyst removing the by-produced hydrogen halide (for example, hydrogen chloride etc.) out of a reaction system, or performed using dehydrohalogenation agent.

As the dehydrohalogenation agent, for example, organic bases such as triethylamine, pyridine, picoline, dimethylaniline, diethylaniline, 1,4-diazabicyclo[2.2.2]octane (DABCO) and 1,8-diazabicyclo[5.4.0]undeca-7-ene (DBU), or inorganic bases such as sodium hydrogencarbonate, sodium carbonate, potassium carbonate, lithium carbonate, sodium hydroxide, potassium hydroxide, calcium hydroxide and magnesium oxide may be mentioned.

Although the amount of the dehydrohalogenation agent used is not limited in particular, it is 0.05 to 10 moles to one mole of the above described sulfur-containing compounds represented by the general formula (2), and preferably 0.1 to 5 moles and more preferably 0.5 to 3 moles.

Next, a method of manufacturing the acrylic ester compound represented by the general formula (1) of the present invention by the dehydrohalogenation of the halopropionic acid ester compound (3) in the presence of abase will be described in detail.

As the base used for this reaction, for example, organic bases such as methylamine, dimethylamine, triethylamine, pyridine, picoline, aniline, dimethylaniline, diethylaniline, toluidine, anisidine, 1,4-diazabicyclo[2.2.2]octane (DABCO) and 1,8-diazabicyclo[5.4.0]undeca-7-ene (DBU), or inorganic bases such as sodium hydrogencarbonate, sodium carbonate, potassium carbonate, lithium carbonate, sodium hydroxide, potassium hydroxide, calcium hydroxide and magnesium oxide may be mentioned.

Although the amount of the base used is not limited in particular, it is 0.05 to 10 moles to one mole of the above described halopropionic acid ester compound (3), and preferably 0.1 to 5 moles and more preferably 0.5 to 3 moles.

The reaction may be performed without solvent or may be performed in a solvent that is inactive to the reaction. The solvent used is not limited in particular if it is an inactive solvent. The reaction may be performed in, for example, water or any organic solvents or a mixture of these solvents.

As the organic solvent, hydrocarbon solvents such as n-hexane, benzene, toluene and xylene, alcoholic solvents such as methanol, ethanol, isopropanol, n-butanol, methoxy ethanol, ethoxyethanol, butoxyethanol, diethyleneglycol monomethyl ether, diethyleneglycol monoethyl ether and diethyleneglycol monobutyl ether, ketone solvents such as acetone, methyl ethyl ketone and methyl isobutyl ketone, ester solvents such as ethyl acetate and butyl acetate, ether solvents such as diethyl ether, diethylene glycol dimethyl ether, tetrahydrofuran and dioxane, halogen solvents such as dichloromethane, chloroform, carbon tetrachloride, 1,2-dichloroethane, tetrachloroethylene, chlorobenzene and o-dichlorobenzene, polar solvents such as acetonitrile, N,N-dimethylformamide, N,N-dimethylacetamide, N,N-dimethylimidazoridinone, dimethyl sulfoxide and sulfolane may be mentioned. These solvents may be used singly or in combination of two or more thereof.

In particular, the reaction temperature is not limited, but is usually −78 to 150° C., preferably −20 to 120° C. and more preferably zero to 100° C.

The reaction time is dependent on the reaction temperature, and, usually it is several minutes to 100 hours, and preferably 30 minutes to 50 hours and more preferably one to 20 hours. Besides, while the rate of a reaction is checked by well-known analytical means (for example, liquid chromatography, gas chromatography, thin layer chromatography, IR, etc.), the reaction may be stopped at an arbitrary rate of a reaction.

In the above described reaction path, a stepwise method may be adopted in which the halopropionic acid ester compound represented by the general formula (3) which is an intermediate may once be taken out the reaction system after the esterification reaction of the halopropionic acid in the first stage, and subsequently the dehydrohalogenation is performed in the second stage, or a one step method may by adopted in which the dehydrohalogenation reaction is performed in one stage (one-pot) without taking out the halopropionic acid ester compound on the way.

In the case where the acrylic ester compound represented by the general formula (1) of the present invention is manufactured, it is preferable to use a polymerization inhibitor in order to prevent the polymerization of a product after the reaction or in the reaction.

As the polymerization inhibitor, for example, various well-known compounds, such as 4-methoxy phenol, 2,6-di-tert-butyl cresol, hydroquinone and phenothiazine, may be mentioned.

Although the amount of the polymerization inhibitor used is not limited in particular, it is usually 0.001 to 5 wt. % to the raw material mixture or the reaction product in the reaction system, preferably 0.05 to 3 wt. % and more preferably 0.01 to 1 wt. %.

After the reaction, the acrylic ester compound represented by the general formula (1) of the present invention that is a reaction product is after-treated by well-known operation and treatment methods (for example, neutralization, solvent extraction, rinsing, separation and solvent evaporation etc.) to be isolated. The acrylic ester compound represented by the general formula (1) obtained by the above described method is further, if required, separated and purified by well-known methods (for example, distillation, recrystallization, chromatography or activated carbon treatment etc.) to be isolated as a compound of higher purity.

The sulfur-containing compound represented by the general formula (2) of the present invention is a novel compound, and is a synthetic intermediate for the acrylic ester compound represented by the general formula (1) as mentioned above.

In the general formula (2), $R_1$, $R_2$, A and X are the same as $R_1$, $R_2$, A and X in the general formula (1) described previously.

As the sulfur-containing compound represented by the general formula (2) of the present invention, for example;

4-mercaptomethyl-1,3-dithiolane,
2-methyl-4-mercaptomethyl-1,3-dithiolane,
2-ethyl-4-mercaptomethyl-1,3-dithiolane
2-n-propyl-4-mercaptomethyl-1,3-dithiolane,
2-n-butyl-4-mercaptomethyl-1,3-dithiolane,
2-phenyl-4-mercaptomethyl-1,3-dithiolane,
2-(4'-methylphenyl)-4-mercaptomethyl-1,3-dithiolane,
2-(3'-methylphenyl)-4-mercaptomethyl-1,3-dithiolane,
2-(2'-methylphenyl)-4-mercaptomethyl-1,3-dithiolane,
2-(4'-tert-butylphenyl)-4-mercaptomethyl-1,3-dithiolane,
2-(4'-methoxyphenyl)-4-mercaptomethyl-1,3-dithiolane,
2-(4'-phenylphenyl)-4-mercaptomethyl-1,3-dithiolane,
2-(4-phenoxyphenyl)-4-mercaptomethyl-1,3-dithiolane,
2-(4'-methylthiophenyl)-4-mercaptomethyl-1,3-dithiolane,
2-(2,4,6-trimethylthiophenyl)-4-mercaptomethyl-1,3-dithiolane, 2-(4'-chlorophenyl)-4-mercaptomethyl-1,3-dithiolane,
2-(4'-bromophenyl)-4-mercaptomethyl-1,3-dithiolane,
2-(α-naphthyl)-4-mercaptomethyl-1,3-dithiolane,
2-(β-naphthyl)-4-mercaptomethyl-1,3-dithiolane,
2,2-dimethyl-4-mercaptomethyl-1,3-dithiolane,
2-methyl-2-phenyl-4-mercaptomethyl-1,3-dithiolane,
2,2-diphenyl-4-mercaptomethyl-1,3-dithiolane,
4-(2-mercaptoethyl)-1,3-dithiolane,
4-(3-mercaptopropyl)-1,3-dithiolane,
4-(2-methyl-2-mercaptoethyl)-1,3-dithiolane,
4-mercaptomethylthiomethyl-1,3-dithiolane,
4-(2-mercaptoethylthio)methyl-1,3-dithiolane,
4-(3-mercaptopropylthio)ethyl-1,3-dithiolane,
4-(2-methyl-2-mercaptoethylthio)methyl-1,3-dithiolane,
4-[2-(mercaptomethylthio)ethyl]-1,3-dithiolane,
4-[2-(2-mercaptoethylthio)ethyl]-1,3-dithiolane,
4-[2-(3-mercaptopropylthio)ethyl]-1,3-dithiolane,
4-[2-(2-methyl-2-mercaptoethylthio)ethyl]-1,3-dithiolane,
4-[3-(mercaptomethylthio)propyl]-1,3-dithiolane,
4-[3-(2-mercaptoethylthio)propyl]-1,3-dithiolane,
4-[3-(3-mercaptopropylthio)propyl]-1,3-dithiolane,
4-[3-(2-methyl-2-mercaptoethylthio)propyl]-1,3-dithiolane,
4-[2-methyl-2-(mercaptomethylthio)ethyl]-1,3-dithiolane,
4-[2-methyl-2-(2-mercaptoethylthio)ethyl]-1,3-dithiolane,
4-[2-methyl-2-(3-mercaptopropylthio)ethyl]-1,3-dithiolane,
4-[2-methyl-2-(2-methyl-2-mercaptoethylthio)ethyl]-1,3-dithiolane,
2-(4-methylphenyl)-4-(2-mercaptoethyl)-1,3-dithiolane,
2-α-naphthyl-4-(3-mercaptopropyl)-1,3-dithiolane,
2-phenyl-4-(mercaptomethylthio)methyl-1,3-dithiolane,
2-(4-methoxyphenyl)-4-(2-mercaptoethylthio)methyl-1,3-dithiolane,
2-(4-bromophenyl)-4-(2-mercaptopropylthio)methyl-1,3-dithiolane,
2-(thiophen-2-yl)-4-(2-methyl-2-mercaptoethylthio)methyl-1,3-dithiolane,
2-furyl-4-[2-(2-mercaptoethylthio)ethyl]-1,3-dithiolane,
2-(4-methylthiophenyl)-4-[3-(mercaptomethylthio)propyl]-1,3-dithiolane,
2-β-naphthyl-4-[2-methyl-2-(mercaptomethylthio)ethyl]-1,3-dithiolane,
2-methyl-4-hydroxymethyl-1,3-dithiolane,
2-phenyl-4-hydroxymethyl-1,3-dithiolane,
2-(4'-methylphenyl)-4-hydroxymethyl-1,3-dithiolane,
2-(4'-methoxyphenyl)-4-hydroxymethyl-1,3-dithiolane,
2-(4'-phenylphenyl)-4-hydroxymethyl-1,3-dithiolane,
2-(4'-phenoxyphenyl)-4-hydroxymethyl-1,3-dithiolane,
2-(4'-methylthiophenyl)-4-hydroxymethyl-1,3-dithiolane,
2-(2,4,6-trimethylthiophenyl)-4-hydroxymethyl-1,3-dithiolane,
2-(4'-chlorophenyl)-4-hydroxymethyl-1,3-dithiolane,
2-(4'-bromophenyl)-4-hydroxymethyl-1,3-dithiolane,
2-(α-naphthyl)-4-hydroxymethyl-1,3-dithiolane,
2-(β-naphthyl)-4-hydroxymethyl-1,3-dithiolane,
2-methyl-2-phenyl-4-hydroxymethyl-1,3-dithiolane,
2,2-diphenyl-4-hydroxymethyl-1,3-dithiolane,
2-(4-methylphenyl)-4-(2-hydroxyethyl)-1,3-dithiolane,
2-α-naphthyl-4-(3-hydroxypropyl)-1,3-dithiolane,
2-phenyl-4-(hydroxymethylthio)methyl-1,3-dithiolane,
2-(4-methoxyphenyl)-4-(2-hydroxyethylthio)methyl-1,3-dithiolane,
2-(4-bromophenyl)-4-(2-hydroxypropylthio)methyl-1,3-dithiolane,
2-(thiophen-2-yl)-4-(2-methyl-2-hydroxyethylthio)methyl-1,3-dithiolane,
2-furyl-4-[2-(2-hydroxyethylthio)ethyl]-1,3-dithiolane,
2-(4-methylthiophenyl)-4-[3-(hydroxymethylthio)propyl]-1,3-dithiolane and 2-β-naphthyl-4-[2-methyl-2-(hydroxymethylthio)ethyl]-1,3-dithiolane may be mentioned, but the present invention is not limited by these exemplary compounds.

The compound whose X is an oxygen atom in the above described general formula (2) is preferably manufactured by a method in which the reaction itself is well-known (for example, a method given in Journal of Chemical Society (C), pages 415–419 (1966), etc.).

Namely, for example, the compound in which $R_1$=hydrogen atom and $R_2$=hydrogen atom, and A is —$CH_2$— group and X is an oxygen atom in the general formula (2) is manufactured by reacting formalin in the presence of an acid catalyst to 2,3-dimercaptopropanol that is a well-known compound.

By the same method a sulfur-containing hydroxy compound whose X is an oxygen atom in the general formula (2) is manufactured by reacting a carbonyl group-containing compound represented by the formula (5) shown below to a dimercapto compound represented by the formula (4) in the presence of an acid catalyst such as a proton acid or a Lewis acid.

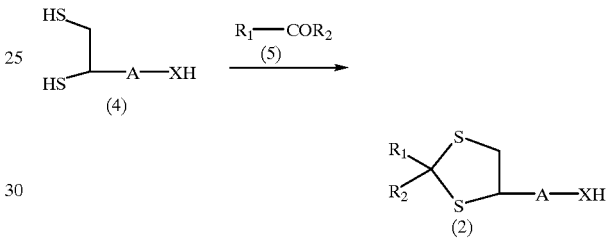

wherein, $R_1$, $R_2$, and A and X are the same as the above.

A sulfur-containing thiol compound whose X is a sulfur atom in the general formula (2) of the present invention is preferably manufactured by transforming a hydroxy group in the molecule into a thiol group using a sulfur-containing hydroxy compound whose X is an oxygen atom in the general formula (2) as a raw material by a method in which the reaction itself is well-known.

Namely, for example, in order to transform the hydroxy compound whose X is an oxygen atom in the general formula (2) into a thiol (mercapto) compound whose for X is a sulfur atom, a well-known method given in, for example, Journal of American Chemical Society, volume 68, pages 2103–2104 (1946), Journal of Organic Chemistry, volume 27, pages 93–95 (1962), Organic Synthesis, V, pages 401–403 (1963), etc.

Accordingly, the thiol compound whose X is a sulfur atom in the general formula (2) of the present invention is preferably manufactured by a method that after transforming a hydroxy compound into a halogenated compound by reacting the hydroxy compound whose X in a general formula (2) is an oxygen atom with hydrogen chloride, hydrogen bromide, etc., thiourea is reacted to this halogenated compound to obtain a thiuronium salt, and then the salt is hydrolyzed using bases, such as aqueous ammonia and sodium hydroxide.

Next, the polymerizable composition containing the acrylic ester compound represented by the general formula (1) of the present invention will be described in detail.

The polymerizable composition of the present invention contains the acrylic ester compound represented by the general formula (1) of the present invention and a polymerization initiator as indispensable components. The polymerization initiator is a compound that can initiate the polymerization of the polymerizable compound by light and/or heat and can be used various well-known polymerization initiator as described below.

In the polymerizable composition of the present invention, the above described acrylic ester compound may be used singly or two or more different acrylic ester compounds encompassed in the general formula (1) may be used in combination.

Furthermore, the polymerizable composition of the present invention may contain well-known polymerizable compounds (a photo- or/and thermal-polymerizable monomer or oligomer), if needed, in addition to the acrylic ester compound represented by the general formula (1) in the range which does not disturb a desired effect of the present invention.

The amount of the acrylic ester compound represented by the general formula (1) contained in the above described polymerizable composition is not limited in particular, but usually, it is preferable no less than 10 wt. % to the weight of the whole polymerizable composition, preferably no less than 20 wt. %, more preferably no less than 30 wt. %, and still more preferably no less than 50 wt. %.

The polymerization initiator used for the polymerizable composition of the present invention is not limited in particular, and various well-known compounds that initiate the polymerization by heat (thermal polymerization initiators) or compounds that initiate the polymerization by irradiating a light (photo polymerization initiators) may be used.

The photopolymerization initiator includes, for example, carbonyl compounds such as benzophenone, 4-methylbenzophenone, 4,4'-dichlorobenzophenone, 2,4,6-trimethylbenzophenone, methyl o-benzoylbenzoate, 4-phenylbenzophenone, 4-(4-methylphenylthio) benzophenone, 3,3-dimethyl-4-methylbenzophenone, 4-(1, 3-acryloyl-1,4,7,10,13-pentaoxatridecyl)benzophenone, 3,3',4,4'-tetra(tert-butylperoxycarbonyl) benzophenone, 4-benzoyl-N,N,N-methylbenzenemethanaminium chloride, 2-hydroxy-3-(4-benzoylphenoxy)-N,N,N-trimethyl-1-propanaminium chloride, 4-benzoyl-N,N-dimethyl-N-[(2-(1-oxo-2-propenoxy)ethyl)benzenemethanaminium chloride, 4-benzoyl-N,N-dimethyl-N-[2-(1-oxo-2-propenyloxy)ethyl]-benzenemethanaminium bromide, 2-isopropylthioisopropylthioxanthone, 4-isopropylthioxanthone, 2,4-dimethylthioxanthone, 2,4-diethylthioxanthone, 2,4-diisopropylthioxanthone, 2,4-dichlorothioxanthone, 1-chloro-4-propoxythioxanthone 2-hydroxy-3-(3,4-dimethyl-9-oxo-9H-thioxanthon-2-yloxy)-N,N,N-trimethyl-1-propanaminium chloride, 2-benzoylmethylene-3-methylnaphtho(1,2-d)thiazoline; dicarbonyl compounds such as benzyl, 1,7,7-trimethylbicyclo[2,2,1]heptane-2,3-dione (common name: camphorquinone), 2-methylanthraquinone, 2-ethylanthraquinone, 2-tert-butylanthraquinone, 1-chloroanthraquinone, 2-amylanthraquinone, 9,10-phenanthlenequinone, methyl a-oxobenzene acetate; acetophenone compounds such as acetophenone, 2-hydroxy-2-methyl-1-phenylpropan-1-one, 1-(4-isopropylphenyl)-2-hydroxy-2-methylpropan-1-one, 1-[4-(2-hydroxyethoxy)phenyl]-2-hydroxy-2-methylpropan-1-one, 1-hydroxycyclohexylphenylketone, dimethoxyacetophenone, diethoxyacetophenone, 2,2-dimethoxy-1,2-diphenylethan-1-one, 2,2-diethoxy-1,2-diphenylethan-1-one, 1,1-dichloroacetophenone, N,N-dimethylaminoacetophenone, 2-methyl-1-(4-methylthiophenyl)-2-morphorinolpropan-1-one, 2-benzyl-2-dimethylamino-1-(4-morphorinophenyl)butan-1-one, 1-phenyl-1,2-propanedione-2-(o-ethoxycarbonyl)oxym, 3,6-bis(2-methyl-2-morphorinopropanoyl)-9-butylcarbazole; benzoin and benzoin ether compounds such as benzoin methyl ether, benzoin ethyl ether, benzoin isopropyl ether, benzoin-n-butyl ether, benzoin isobutyl ether; aryl phosphine oxide compounds such as 2,4,6-trimethylbenzoyldiphenylphosphine oxide, bis(2,6-dichlorobenzoyl)-(4-n-propylphenyl)phosphine oxide; aminocarbonyl compounds such as methyl 4-dimethylaminobenzoate, ethyl 4-dimethylaminobenzoate, 4-dimethylaminobenzoate-n-butoxyethyl ester, isoamyl 4-dimethylaminobenzoate, benzoate-2-dimethylaminoethyl ester, 4,4'-bis(dimethylamino)benzophenone (Michler's ketone), 4,4'-bis(diethylamino)benzophenone, 2,5'-bis(4-dimethylaminobenzal)cyclopentanone; halogenated compounds such as 2,2,2-trichloro-1-(4'-tert-butylphenyl)ethan-1-one, 2,2-dichloro-1-(4-phenoxyphenyl)ethan-1-one, a,a,a-tribromomethylphenylsulfone, 2,4,6-tris(trichloromethyl) triazine, 2,4-bis(trichloromethyl)-6-(4-methoxyphenyl) triazine, 2,4-bis(trichloromethyl)-6-(4-methoxystyryl) triazine, 2,4-bis(trichloromethyl)-6-(3,4-methylenedioxyphenyl)triazine), 2,4-bis(trichloromethyl)-6-(4-methoxynaphthyl)triazine, 2,4-bis(trichloromethyl)-6-[2-(5-methylfuryl)etylidyne]triazine, 2,4-bis (trichloromethyl)-6-[2-furyletylidyne]triazine; other well-known compounds such as 9-phenylacridine, 2,2'-bis(o-chlorophenyl)-4,4',5,5'-tetraphenyl-1,2-biimidazole, 2,2-azobis(2-aminopropane)dihydrochloride, 2,2-azobis[2-(imidazolin-2-yl)propanel dihydrochloride, η-5-2-4-(cyclopentadienyl)(1,2,3,4,5,6,η)-(methylethyl)benzene] iron(II) hexafluorophosphate, bis(5-cyclopentadienyl)bis[2, 6-difluoro-3-(1H-pyr-1-yl)phenyl]titanium. These may be used singly or in combination of two or more thereof.

The amount of this photo polymerization initiator used is 0.001 to 50 weight parts to 100 weight parts of the acrylic ester compound represented by the general formula (1), preferably 0.01 to 30 weight parts, more preferably 0.1 to 10 weight parts and still more preferably 0.2 to 5 weight parts.

As the thermal polymerization initiator, for example, peroxides such as benzoyl peroxide, p-chlorobenzoyl peroxide, diisopropyl peroxy carbonate, di-2-ethylhexyl peroxy carbonate and tert-butyl peroxy pivalate, and azo compounds such as zobisisobutylonitrile, etc. may be mentioned.

The amount of the thermal polymerization initiator used is usually 0.001 to 50 weight parts to 100 weight parts of the acrylic ester compound represented by the general formula (1), preferably 0.01 to 30 weight parts, more preferably 0.1 to 10 weight parts and still more preferably 0.2 to 5 weight parts.

Well-known polymerizable compounds other than the acrylic ester compound represented by the general formula (1) as a polymerizable compound used for the polymerizable composition of the present invention include, for example, mono functional acrylates such as methyl (meth)acrylate, butyl (meth)acrylate, 2-ethylhexyl (meth)acrylate, ethyl Carbitol (meth)acrylate, lauryl (meth)acrylate, tetracyclododecyl (meth)acrylate, phenoxyethyl (meth)acrylate, nonylphenoxyethyl (meth)acrylate, dicyclopentenyl (meth)acrylate, isobornyl (meth)acrylate, N-n-butyl-O-(meth)acryloyloxy ethylcarbamate, acryloyl morpholine, trifluoroethyl (meth)acrylate, tribromobenzyl (meth) acrylate and perfluorooctylethyl (meth)acrylate;

bifunctional (meth)acrylates such as ethyleneglycol di(meth)acrylate, propyleneglycol di(meth)acrylate, neopentylglycol di(meth)acrylate, 1,6-hexanediol di(meth) acrylate, triethylenglycol di(meth)acrylate, tripropyleneglycol di(meth)acrylate, polyethylene glycol di(meth) acrylate, polypropylene glycol di(meth)acrylate, 2,2-bis(4-acryloxy phenyl)propane, 2,2-bis(4-methacryloyloxyphenyl)propane, bis(4-acryloyloxyphenyl)methane, bis(4-methacryloyloxy phenyl)methane, 4,4'-bis(2-acryloyloxy)phenyl sulfide, 4,4'-bis (2-methacryloyloxy)phenyl sulfide, 2,2-bis(4-acryloyloxyethoxyphenyl)propane, 2,2-bis(4-methacryloyloxyethoxyphenyl)propane, 2,2-bis[4-(2-acryloyloxypropoxy)phenyl]propane, 2,2-bis[4-(2-methacryloyloxypropoxy)phenyl]propane, bis(4-acryloyloxyethoxyphenyl)methane, bis(4-methacryloyloxyethoxyphenyl)methane, bis[4-(2-acryloyloxypropoxy)phenyl]methane, [4-(2-methacryloyloxypropoxy)phenyl]methane, 4,4'-bis(2-acryloyloxy ethoxy)phenyl sulfide, 4,4'-bis(2-methacryloyloxyethoxy)phenyl sulfide, 4,4'-bis(2-acryloyloxypropoxy)phenyl sulfide, 4,4'-bis(2-methacryloyloxypropoxy)phenyl sulfide, 4,4'-bis(2-acryloyloxyethoxy)phenyl sulfone, 4,4'-bis(2-methacryloyloxyethoxy)phenyl sulfone, 4,4'-bis(2-acryloyloxypropoxy)phenyl sulfone, 4,4'-bis(2-methacryloyloxypropoxy)phenyl sulfone;

multifunctional acrylates such as trimethylolpropane tri (meth) acrylate, dipentaerythritol pentaacrylate, pentaerythritol triacrylate, pentaerythritol tetraacrylate, ditrimethylol tetraacrylate, dipentaerythritol hexaacrylate, 2-(meth)acryloyloxyethyl trisisocyanurate, (meth)acryloxypropyl tris(methoxy) silane;

epoxy (meth) acrylates that is obtained by reacting (meth) acrylic acid compound to monofunctional or bifunctional epoxy compound, such as phenyl glycidyl ether, ethyleneglycol diglycidyl ether, propyleneglycol diglycidyl ether, resorcin diglycidyl ether, hydroquinone diglycidyl ether, bis(4-hydroxyphenyl)methane (common name, bisphenol F) diglycidyl ether, 2,2-bis (4-hydroxyphenyl) propane (common name, bisphenol A)diglycidyl ether, 4,4'-bishydroxyphenyl sulfide diglycidyl ether, 4,4'-bishydroxyphenyl sulfone (common name, Bisphenol S) diglycidyl ether, 4,4'-biphenol diglycidyl ether, 3,3',5,5'-tetramethyl-4,4'-biphenol diglycidyl ether, tris(2,3-epoxypropyl)isocyanurate;

epoxy (meth)arcylates that is obtained by reacting (meth) acrylic acid compounds to epoxy resins such as phenol novolak type epoxy resin, cresol novolak type epoxy resin, phenol xyloc type epoxy resin, bisphenol type epoxy resin;

vynyl compounds, such as vinylbenzene, divinylbenzene, trivynylbenzene, isopropenylbenzene, diisopropenylbenzene, triisopropenylbenzene, N-vinylpyrolidone, N-vinylcaprolactam;

various kinds of well-known polymerizable monomer, such as allyl group-containing compounds such as ethylene glycol diallyl carbonate, trimellitic acid triallyl ester, triallyl isocyanurate; or various kinds of well-known polymerizable oligomer, such as polyurethane (meth)acrylates, epoxy(meth)acrylates, polyester (meth)acrylates and polyether (meth)acrylates.

The use amount of these polymerizable compounds is usually no more than 300 weight parts to 100 weight parts of the acrylic ester compound represented by the general formula (1) to attain the effect of the present invention preferably no more than 200 weight parts and more preferably no more than 100 weight parts.

Specifically, a polymerizable composition of the present invention is obtained using the acrylic ester compound represented by the general formula (1) of the present invention and the various above described well-known polymerizable compounds by request, and mixing and dissolving an obtained mixture after further adding the above described polymerization initiator. The polymerizable composition is used for polymerization and curing, after insoluble matter, foreign matter, etc. are removed by filtration and are fully further degassed under reduced pressure before polymerization if needed.

Besides, in the case where the polymerizable composition is manufactured, various well-known additives, such as internal mold releasing agent, photostabilizer, UV absorber, antioxidant, coloring pigments (for example, cyanine green, cyanine blue, etc.), dyestuff, flow modifier and inorganic fillers (for example, talc, silica, alumina, barium sulfate, magnesium oxide, etc.), may be added according to request.

Cured articles and optical components that comprise the cured articles of the present invention are obtained by polymerizing and curing the above described polymerizable composition. Various conventionally well-known methods are adopted and performed preferably as the methods of the present invention and typically and, for example, a cast polymerization using radical polymerization reaction is mentioned that is started by heat or light after the polymerizable composition obtained as mentioned above is poured into a mold.

The mold is constituted by two mirror finished mold dies through gaskets that consist of polyethylene, ethylene-vinyl acetate copolymer and polyvinyl chloride, etc. As the mold dies, the mold dies of combination of glass and glass; plastics plate and glass; glass and metal plate; etc. are mentioned. Besides, except that the above described soft thermoplastic resins (polyethylene, ethylene-vinyl acetate copolymer and polyvinyl chloride, etc.) are used as a gasket, two mold dies may be fixed with polyester tacky adhesion tape etc. Besides, the well-known treatment method, such as mold release treatment, may be applied to the mold die.

As a radical polymerization reaction, as mentioned above, method of using polymerization reaction by heat (thermal polymerization), polymerization reaction by light, such as ultraviolet radiation (photo polymerization), polymerization reaction by γ rays, etc. or method in which these methods are combined together may be mentioned.

When polymerization by light is performed, after curing the cured article that is obtained by being removed from the mold die, or the optics that consist of this cured article may be annealed in order to remove internal stress and distortion.

In these methods, although curing in thermal polymerization requires several hours to dozens of hours, curing in photo polymerization by ultraviolet radiation etc., can be finished in only several seconds to several minutes. Therefore, when in view of raising manufacturing productivity of the optics of the present invention, a photo polymerization method is preferable.

In case of thermal polymerization, since a polymerization temperature is influenced by a polymerization condition, such as a kind of polymerization initiator, it is not limited, but is usually 25 to 200° C. and preferably 50 to 170° C.

As a molding method of optical lens, as mentioned above, a method of obtaining lens by applying a casting polymerization with light or/and heat may be mentioned (for example, Japanese Patent Laid-Open Nos. 60-135901, 10-67736, 10-130250, etc.).

Accordingly, this method is preferably performed in the way that after the polymerizable composition containing acrylic ester compound represented by the general formula (1) of the present invention that is manufactured by the above described method receives degassing by a suitable method if needed, it is poured into a mold, and then polymerized usually by light irradiation. Besides, in case of polymerization by heat, this method is preferably performed in the way that the composition is gradually heated from low temperature to high temperature to be polymerized.

Annealing treatment may be performed to obtained optical lens after curing if needed. Furthermore, for the purpose of providing antireflection, high hardness, wear-resistance, anti-fog property or fashionability, if needed, well-known various kinds of physical or chemical treatment, such as, surface polishing, antistatic treatment, hard coating, non-reflective coating, dyeing, light control treatment (for example, photochromic lens treatment etc.) may be applied.

As molding method of a base plate for optical disc or magneto-optical disc, for example, a conventionally well-known method, such as, a method in which the polymerizable composition containing acrylic ester compound represented by the general formula (1) obtained by the above described method is poured into a mold cavity for disk base plate, and then polymerized by the radical polymerization method etc., and if required heated afterwards (Japanese Patent Laid-Open Nos. 58-130450, 58-137150, 62-280008, etc.), a method in which photo polymerization is performed within double-sided glass mold (Japanese Patent Laid-Open No. 60-202557) and a method in which a liquid resin is polymerized by heat under pressurized condition after cast or injected (Japanese Patent Laid-Open No. 60-203414) etc. may be mentioned.

The cured articles obtained by photo polymerization of the above described polymerizable composition of the present invention and the optical components comprising the cured articles require polymerization and curing time of several minutes to several hours, and they can be polymerized and molded in a shorter time as compared with existing thermosetting resin for optical components represented by poly diethyleneglycol diallylcarbonate and polythiourethane, and provide an advantage of high productivity.

Furthermore, the cured article of the present invention and the optical components have advantages of excellent transparency, mechanical property and thermal property, and also a higher refractive index as compared with well-known photo polymerizable monomer. For the use of the optical components, various plastic lenses represented by a spectacles lens for correction, a base plate for an optical information recording medium, a plastics base plate for liquid crystal cells, optical fiber coating material, etc. may be mentioned as practical embodiments, for example.

The (meth)acrylic ester compound represented by the general formula (1) of the present invention is a new compound which has cyclic thioacetal structure in molecule, and is very useful compound as a resin raw material monomer for optical components represented by spectacles lens for correction etc.

Although hereinafter the present invention will be described still more in detail using examples, the present invention is not limited to these examples.

(1) Synthesis of Sulfur-Containing Compound Represented by the General Formula (2)

MANUFACTURING EXAMPLE 1

[Synthesis of 4-hydroxymethyl-1,3-dithiolane]

Manufacturing was performed according to the method given in Journal of Chemical Society (C), pages 415–419 (1966). That is, 250 ml of 30% formaldehyde aqueous solution and 250 ml of dioxane were measured and poured into one-liter glass reactor equipped with a stirrer and a cooling pipe, and then 186 g (1.5 moles) of 2,3-dimercaptopropanol was added to the mixture with stirring. After one gram of sulfuric acid was further added, the mixture was reacted with heating and stirring at 90 to 100° C. for six hours under nitrogen atmosphere. After checked by gas chromatography that raw material disappeared and the reaction was completed, the solvent was evaporated off under reduced pressure. After extraction by chloroform and rinsing with water, the solvent was evaporated off from the organic layer and 133 g (0.98 moles) of 4-hydroxymethyl-1,3-dithiolane was obtained.

Yield: 65% Purity: >99% (area method by a gas chromatography analysis) Boiling point: 124–125° C./266 kPa (2 mmHg) EI-MS: 136(M)

Example 1

[Synthesis of 4-mercaptomethyl-1,3-dithiolane: a Compound in which $R_1$=Hydrogen Atom, $R_2$=Hydrogen Atom, A=—$CH_2$— Group and X=Sulfur Atom in the General Formula (2)]

Thiourea 38.0 g (0.50 moles) and 88 g of 48% hydrobromic acid (an equivalent for hydrogen bromide 0.5 moles) were introduced into a 500 ml glass reactor equipped with a stirrer and a cooling pipe. Into the mixture 68 g (0.50 moles) of 4-hydroxymethyl-1,3-dithiolane that was synthesized in Manufacturing Example 1 was added dropwise over 35 minutes at 60° C. Furthermore, it was reacted at 80° C. for 4 hours, and a thiuronium salt was obtained. Reaction solution was analyzed by high-speed liquid chromatography, after it was checked that hydroxy compound of raw material had disappeared, 300 g of 18% aqueous ammonia was added dropwise over 10 minutes to the reaction mixture at 50° C. The reaction was further continued at 50° C. for two hours and thiuronium salt was hydrolyzed. Toluene 200 g was added, and after separated and extracted the toluene layer was rinsed with water until wastewater layer became neutral. Then, the toluene layer was taken out of the reaction system, toluene was evaporated off under reduced pressure at 40° C., and a crude product of a yellow transparent liquid was obtained. This crude product was purified by silica gel column chromatography (toluene is used as a solvent), and 61 g (0.40 moles) of 4-mercaptomethyl-1,3-dithiolane that was a colorless liquid shown in the following formula (2-1) was obtained.

Yield: 80% Purity: >99% (area method by gas chromatography analysis) EI-MS: 152(M)

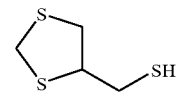

(2-1)

Example 2

[Synthesis of 2-phenyl-4-hydroxymethyl-1,3-dithiolane: a Compound in which $R_1$=Phenyl Group, $R_2$=Hydrogen Atom, A=—$CH_2$— Group and X=Sulfur Atom in the General Formula (2)]

Into one-liter glass reactor equipped with a stirrer and a cooling pipe, 50.0 g (0.40 moles) of 2,3-dimercaptopropanol, 0.44 g (0.004 moles) of 98% sulfuric acid and 80 g of dioxane were weighed and poured, and 46.8 g (0.442 moles) of benzaldehyde was added dropwise over 30 minutes at 25° C. to the mixture. Furthermore, the mixture was reacted with stirring to finish the reaction at 70° C. for five hours, and the mixture was poured into 500 g of water and then was extracted by toluene. An organic layer (toluene solution) was rinsed and separated with water repeatedly until the water layer became neutral and then the organic layer was taken out. After toluene was evaporated off to concentrate the mixture under reduced pressure, n-hexane was added. The solution was kept standing, and precipitated crystal was filtrated and taken out. Furthermore, the crystal was washed by toluene/hexane (weight ratio=60/40), and 72.2 g of 2-phenyl-4-hydroxymethyl-1,3-dithiolane shown in the following formula (2-2) were obtained as a white crystal.

Yield: 85% Purity: 99% (calculated by the gas chromatograph area percentage method) 270 MHz $^1$H-NMR δ (CDCl$_3$): 2.25 (t, 1H), 3.40 to 4.20 (m, 5H), 5.65 (d, 1H), and 7.20 to 7.55 (5H) EI-MS: 212(M)

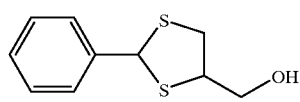

(2-2)

Example 3

[Synthesis of 2-(α-naphtyl)-4-hydroxymethyl-1,3-dithiolane: a Compound in which R$_1$=α-naphtyl Group, R$_2$=Hydrogen Atom, A=—CH$_2$— Group and X=Oxygen Atom in the General Formula (2)]

The same method was followed as in Example 2 except that α-formylnaphthalene was used in stead of benzaldehyde in Example 2 to obtain 2-(α-naphtyl)-4-hydroxymethyl-1,3-dithiolane represented by the following formula (2-3).

EI-MS: 262(M)

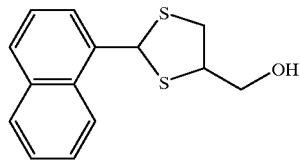

(2-3)

Example 4

[Synthesis of 2-(β-naphtyl)-4-hydroxymethyl-1,3-dithiolane: a Compound in which R$_1$=β-naphtyl Group, R$_2$=Hydrogen Atom, A=—CH$_2$— Group and X=Oxygen Atom in the General Formula (2)]

The same method was followed as in Example 2 except that β-formylnaphthalene was used in stead of benzaldehyde in Example 2 to obtain 2-(β-naphtyl)-4-hydroxymethyl-1,3-dithiolane represented by the following formula (2-4).

EI-MS: 262(M)

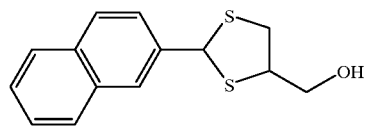

(2-4)

Example 5

[Synthesis of 2-(thiophen-2-yl)-4-hydroxymethyl-1,3-dithiolane: a Compound in which R$_1$=Thiophen-2-yl Group, R$_2$=Hydrogen Atom, A=—CH$_2$— Group and X=Oxygen Atom in the General Formula (2)]

The same method was followed as in Example 2 except that 2-formylthiophene was used in stead of benzaldehyde in Example 2 to obtain 2-(thiophen-2-yl)-4-hydroxymethyl-1,3-dithiolane represented by the following formula (2-5).

EI-MS: 218(M)

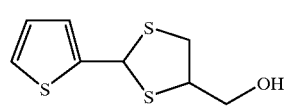

(2-5)

Example 6

[Synthesis of 2-phenyl-4-mercaptomethyl-1,3-dithiolane: a Compound in which R$_1$=Phenyl Group, R$_2$=Hydrogen Atom, A=—CH$_2$— Group and X=Sulfur Atom in the General Formula (2)]

The same method was followed as in Example 1 except that 2-phenyl-4-hydroxymethyl-1,3-dithiolane produced in Example 2 was used in stead of 4-hydroxymethyl-1,3-dithiolane synthesized in Manufacturing Example 1 to obtain 2-phenyl-4-mercaptomethyl-1,3-dithiolane represented by the following formula (2-6).

270 MHz, $^1$H-NMR δ (CDCl$_3$): 1.68 (dt, 1H), 2.80 to 3:58 (m, 4H), 3.97 (dm, 1H), 5.65 (d, 1H), 7.20 to 7.53 (5H) EI-MS: 228(M)

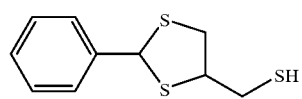

(2-6)

Example 7

[Synthesis of 2-(α-naphtyl)-4-mercaptomethyl-1,3-dithiolane: a Compound in which R$_1$=α-naphtyl Group, R$_2$=Hydrogen Atom, A=—CH$_2$— Group and X=Sulfur Atom in the General Formula (2)]

The same method was followed as in Example 1 except that 2-(α-naphtyl)-4-hydroxymethyl-1,3-dithiolane produced in Example 3 was used in stead of 4-hydroxymethyl-1,3-dithiolane synthesized in Manufacturing Example 1 to obtain 2-(α-naphtyl)-4-mercaptomethyl-1,3-dithiolane represented by the following formula (2-7).

EI-MS: 278(M)

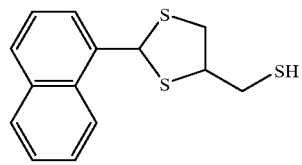

(2-7)

Example 8

[Synthesis of 2-(β-naphtyl)-4-mercaptomethyl-1,3-dithiolane: a Compound in which R$_1$=β-naphtyl Group, R$_2$=Hydrogen Atom, A=—CH$_2$— Group and X=Sulfur Atom in the General Formula (2)]

The same method was followed as in Example 1 except that 2-(β-naphtyl)-4-hydroxymethyl-1,3-dithiolane produced in Example 4 was used in stead of 4-hydroxymethyl-1,3-dithiolane synthesized in Manufacturing Example 1 to obtain 2-(β-naphtyl)-4-mercaptomethyl-1,3-dithiolane represented by the following formula (2-8).

EI-MS: 278(M)

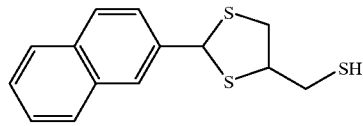

(2-8)

Example 9

[Synthesis of 2-(thiophen-2-yl)-4-mercaptomethyl-1,3-dithiolane: a Compound in which $R_1$=thiophen-2-yl Group, $R_2$=Hydrogen Atom, A=—$CH_2$— Group and X=Sulfur Atom in the General Formula (2)]

The same method was followed as in Example 1 except that 2-(thiophen-2-yl)-4-hydroxymethyl-1,3-dithiolane produced in Example 5 was used in stead of 4-hydroxymethyl-1,3-dithiolane synthesized in Manufacturing Example 1 to obtain 2-(thiophen-2-yl)-4-mercaptomethyl-1,3-dithiolane represented by the following formula (2-9).

EI-MS: 234(M)

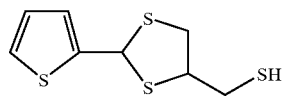

(2-9)

(2) Synthesis of Acrylic Ester Compound Represented by the General Formula (1)

Example 10

[Synthesis of 4-acryloylthiomethyl-1,3-dithiolane: a Compound in which $R_1$=Hydrogen Atom, $R_2$=Hydrogen Atom, $R_3$=Hydrogen Atom, A=—$CH_2$— Group and X=Sulfur Atom in the General Formula (1)]

Into 500 ml glass reactor equipped with a stirrer and a cooling pipe, 91.2 g (0.60 moles) of 4-mercaptomethyl-1,3-dithiolane (2-1) produced in Example 1 was weighed and poured, and 80.0 g (0.63 moles) of 3-chloropropionic chloride was added dropwise into the reactor at 40° C. over 15 minutes. After reacted at 40° C. for eight hours with stirring, 200 g of toluene was added to the reaction mixture to dissolve the mixture. The mixture then was moved into a separating funnel to be rinsed three times with 300 g of 3 wt. % sodium hydrogen carbonate aqueous solution. Then, after the mixture was rinsed with 300 g of pure water until the water layer became neutral, the organic layer (toluene solution) was taken out. Toluene was evaporated off under reduced pressure, and 119 g of 4-(3-chloropropionylthiomethyl)-1,3-dithiolane was obtained as a transparent and colorless liquid.

Subsequently, 119 g (0.49 moles) of 4-(3-chloropropionylthiomethyl)-1,3-dithiolane obtained as mentioned above and 200 g of acetone were introduced into one-liter glass reactor to obtain a solution. To the solution, 74 g (0.73 moles) of triethylamine was added dropwise at 25° C. over one hour. Then, after stirred and reacted at 25° C. for six hours, 400 g of toluene and 400 g of water were added to the reaction mixture. After separated and extracted a toluene layer was taken out. After rinsed with 5 wt. % hydrogen chloride aqueous solution, the toluene solution was rinsed with water until the water layer becomes neutral. Then toluene was evaporated off under a reduced pressure, and 99 g (0.48 moles) of 4-(2'-acryloylthiomethyl)-1,3-dithiolane represented by the following formula (1-1) was obtained as a viscous transparent and colorless liquid.

Yield: 80%

Purity: >99% (area method by liquid chromatography analysis)

EI-MS: 206(M)

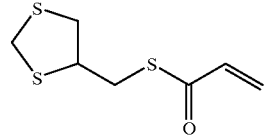

(1-1)

Example 11

[Synthesis of 2-phenyl-4-acryloylthiomethyl-1,3-dithiolane: a Compound in which $R_1$=Phenyl Atom, $R_2$=Hydrogen Atom, $R_3$=Hydrogen Atom, A=—$CH_2$— Group and X=Sulfur Atom in the General Formula (1)]

The same method was followed as in Example 10 except that 2-phenyl-4-mercaptomethyl-1,3-dithiolane (2-6) produced in Example 6 was used in stead of 4-mercaptomethyl-1,3-dithiolane (2-1) produced in Example 1 as reaction material to obtain 2-phenyl-4-acryloylthiomethyl-1,3-dithiolane represented by the following formula (1-2).

270 MHz $^1$H-NMR δ(CDCl$_3$): 3.22 to 3.55 (m, 4H), 4.08 (dm, 1H), 5.68 to 5.77 (m, 2H), 6.35 to 6.40 (d, 2H), 7.25 to 7.55 (5H) EI-MS: 282(M)

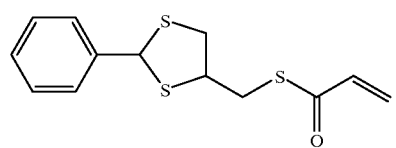

(1-2)

Viscosity of this compound was measured to obtain below 200 mPa·s (200 cPoise). This compound could flow easily with comparatively low viscosity, and had an easy handling at the time of work such as filtration and transport etc.

Example 12

[Synthesis of 2-(α-naphthyl)-4-acryloylthiomethyl-1,3-dithiolane: a Compound in which $R_1$=α-naphthyl Group, $R_2$=Hydrogen Atom, $R_3$=Hydrogen Atom, A=—$CH_2$— Group and X=Sulfur Atom in the General Formula (1)]

The same method was followed as in Example 10 except that 2-(α-naphthyl)-4-mercaptomethyl-1,3-dithiolane (2-7) produced in Example 7 was used in stead of 4-mercaptomethyl-1,3-dithiolane (2-1) produced in Example 1 as reaction material to obtain 2-(α-naphthyl)-4- acryloylthiomethyl-1,3-dithiolane represented by the following formula (1-3).

EI-MS: 332(M)

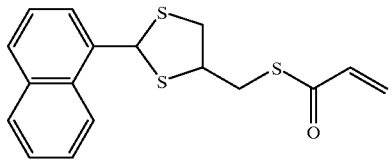

(1-3)

Example 13

[Synthesis of 2-(β-naphthyl)-4-acryloylthiomethyl-1,3-dithiolane: a Compound in which $R_1$=β-naphthyl Group, $R_2$=Hydrogen Atom, $R_3$=Hydrogen Atom, A=—$CH_2$— Group and X=Sulfur Atom in the General Formula (1)]

The same method was followed as in Example 10 except that 2-(β-naphthyl)-4-mercaptomethyl-1,3-dithiolane (2-8) produced in Example 8 was used in stead of 4-mercaptomethyl-1,3-dithiolane (2-1) produced in Example 1 as reaction material to obtain 2-(β-naphthyl)-4-acryloylthiomethyl-1,3-dithiolane represented by the following formula (1-4).

EI-MS: 332(M)

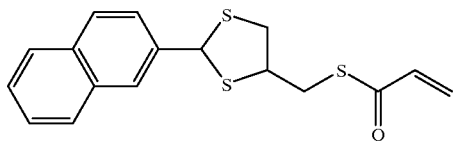

(1-4)

Example 14

[Synthesis of 2-(thiophen-2-yl)-4-acryloylthiomethyl-1,3-dithiolane: a Compound in which $R_1$=Thiophen-2-yl Group, $R_2$=Hydrogen Atom, $R_3$=Hydrogen Atom, A=—$CH_2$— Group and X=Sulfur Atom in the General Formula (1)]

The same method was followed as in Example 10 except that 2-(thiophen-2-yl)-4-mercaptomethyl-1,3-dithiolane (2-9) produced in Example 9 was used in stead of 4-mercaptomethyl-1,3-dithiolane (2-1) produced in Example 1 as reaction material to obtain 2-(thiophen-2-yl)-4-acryloylthiomethyl-1,3-dithiolane represented by the following formula (1-5).

EI-MS: 288(M)

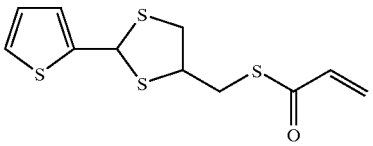

(1-5)

Example 15

[Synthesis of 2-phenyl-4-acryloyloxymethyl-1,3-dithiolane: a Compound in which $R_1$=Phenyl Group, $R_2$=Hydrogen Atom, $R_3$=Hydrogen Atom, A=—$CH_2$— Group and X=Oxygen Atom in the General Formula (1)]

The same method was followed as in Example 10 except that 2-phenyl-4-hydroxymethyl-1,3-dithiolane (2-2) produced in Example 2 was used in stead of 4-mercaptomethyl-1,3-dithiolane (2-1) produced in Example 1 as reaction material to obtain 2-phenyl-4-acryloyloxymethyl-1,3-dithiolane represented by the following formula (1-6).

270 MHz $^1$H-NMR δ ($CDCl_3$): 3.30 to 3.55 (m, 2H), 4.00 to 4.55 (m, 3H), 5.75 (s, 1H), 5.85 to 5.90 (dd, 1H), 6.10 to 6.20 (dd, 1H), 6.40 to 6.50 (d, 1H), 7.20 to 7.60 (5H) EI-MS: 266(M)

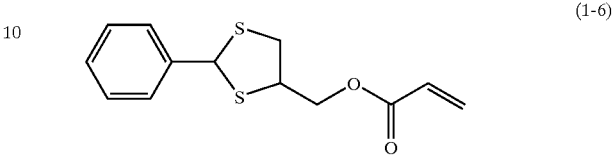

(1-6)

(3) Manufacturing of a Polymerizable Composition using the Acrylic Ester Compound Represented by the General Formula (1) and Manufacturing of a Cured Article by Curing the Composition.

Physical properties evaluation (transparency, thermal property, mechanical property) of the cured articles or optical components (lens) manufactured in the following Examples and the Comparative Examples was performed by the following methods.

Appearance: Color and transparency were evaluated by visual inspection.

Refractive index and Abbe number: They were measured at 20° C. using the Pulfrich refractometer.

Heat resistance: Glass transition temperature of a cured article was measured using TMA (the needle inserting method).

Impact resistance: From a height of 127 cm, an iron ball of 28.7 g was dropped onto the central part of a minus lens with a central thickness of 1.5 mm, and the existence of a crack was investigated.

Example 16

To 30 g of acrylic ester compounds (4-acryloylthiomethyl-1,3-dithiolane) obtained in the above described Example 10, 150 mg of 2-hydroxy-2-methyl-1-phenylpropan-1-one ("Darocur-1173", registered trademark Ciba Specialty Chemicals) was added as a photopolymerization initiator, and mixed well and dissolved. After the obtained liquid was fully degassed under reduced pressure, it was poured into a mold die that consists of glass molds and a gasket. Ultraviolet rays were irradiated for 60 seconds using a metal halide lamp (80 W/cm), and polymerization was performed. The cured article that was cooled gradually and molded was taken out from the molds after the polymerization was performed.

The obtained cured article was transparent and colorless, and optical distortion was not observed. Refractive index (nd) was 1.660 and Abbe number was 36 (vd).

Examples 17 to 21

The same method was followed as in Example 16 except that the acrylic ester compounds produced in the above described Examples 11 to 15 were used in stead of the acrylic ester compound (4-acryloylthiomethyl-1,3-dithiolane) obtained in Example 10, and 2,4,6-trimethoxybenzoyl diphenylphosphineoxide (manufactured by BASF A.G.) was used as a photopolymerization initiator instead of 2-hydroxy-2-methyl-1-phenylpropan-1-one to prepare the polymer compositions and to perform polymerization and curing.

The result of the measured refractive index and the Abbe number of the cured articles are shown in the following Table 1.

TABLE 1

| Example | Used acrylic ester compound | Refractive index (nd) | Abbe number (vd) |
|---|---|---|---|
| 17 | 2-phenyl-4-acryloylthiomethyl-1,3-dithiolane (manufactured in Example 11) | 1.688 | 30.5 |
| 18 | 2-(α-naphthyl)-4-acryloylthiomethyl 1,3-dithiolane (manufactured in Example 12) | 1.693 | 29.5 |
| 19 | 2-(β-naphthyl)-4-acryloylthiomethyl 1,3-dithiolane (manufactured in Example 13) | 1.693 | 29.5 |
| 20 | 2-(thiophen-2-yl)-4-acryloylthiomethyl-1,3-dithiolane (manufactured in Example 14) | 1.695 | 29.5 |
| 21 | 2-phenyl-4-acryloyloxymethyl-1,3-dithiolane (manufactured in Example 15) | 1.653 | 32.2 |

The polymerizable compositions containing the acrylic ester compound of the present invention can be polymerized and cured in a short time by a polymerization reaction started with optical irradiation, and a refractive index of the cured article obtained is very high.

Example 22

As a photopolymerization initiator, 30 mg of 2,4,6-trimethylbenzoyl diphenyl phosphine oxide (manufactured by BASF A.G.) was added to a mixture obtained by mixing 24 g of the acrylic ester compound obtained in the above-mentioned example 11 (2-phenyl-4-acryloylthiomethyl-1,3-dithiolane), 3 g of trimethylolpropane trimethacrylate and 3 g of bisphenol A diglycidylether dimethacrylate, and the mixture obtained was mixed well and dissolved to prepare a liquid polymerizable composition with low viscosity. After the obtained composition is degassed sufficiently under reduced pressure it was poured into a mold die which consists of glass molds and a gasket. Ultraviolet rays were irradiated for 60 seconds using a metal halide lamp (120 W/cm), and polymerization was performed. Then, after cooling gradually to room temperature, the cured article was taken out from the mold, and it was further heated at 130° C. for two hours in an inert oven to be annealed.

Obtained cured article was transparent and colorless, and optical distortion was not observed. Refractive index (nd) was 1.655 and Abbe number was 33 (vd).

A glass transition temperature of the cured article was enough for a grade of practical use as a glasses lens for vision correction, and had excellent shock resistance.

Comparative Example 1

The same method was followed as in Example 22 except that a conventionally known acrylic ester compound (described in Japanese Patent Laid-Open No. 3-217412) of 24 g of 1,4-bis(2-methacryloyloxyethylthio)xylylene and 6 g of 2,2-bis(4-methacryloyloxyethoxyphenyl)propane were used instead of the acrylic ester compound represented by the general formula (1) of the present invention as a polymerizable compound to prepare a polymerizable composition, and a lens was manufactured.

The lens was transparent and colorless, and refractive index (nd) was 1.588 and Abbe number (vd) was 39.

Comparative Example 2

The same method was followed as in Example 22 except that a conventionally known compound (described in Japanese Patent Laid-Open No.3-215801) of 2-methacryloyloxymethyl-1,4dithiane was used instead of the acrylic ester compound represented by the general formula (1) of the present invention as a polymerizable compound to obtain a cured article. The cured article was transparent and colorless, and refractive index (nd) was 1.590 and Abbe number (vd) was 43.

Comparative Example 3

The same method was followed as in Example 22 except that a conventionally known compound (a compound described in page 61 of the specification of Japanese Patent Laid-open Publication of International Patent Application No. 2000-509075) of 6-methacryloyloxy-1,4-dithiacycloheptane was used instead of the acrylic ester compound represented by the general formula (1) of the present invention as a polymerizable compound to obtain a polymerizable composition, and a cured article was manufactured. The cured article was transparent and colorless, a refractive index (nd) was 1.545 and Abbe number (vd) was 43.5.

Since the acrylic ester compound of the present invention has a lower viscosity as compared with conventionally known monomer, when preparing polymerizable composition and when manufacturing optical components using the polymerizable composition, it has an excellent fluidity and workability in handling.

Moreover, the polymerizable composition containing the acrylic ester compound of the present invention may be polymerized and cured in a short time by a compound that starts polymerization by optical irradiation (polymerization initiator). Therefore a cured article or an optical component such as lenses may be obtained with excellent production efficiency. The cured article or the lens obtained has excellent physical properties in practical use, such as heat resistance and shock resistance, and has a higher refractive index as compared with conventionally known acrylic ester compounds.

What is claimed is:

1. An acrylic ester compound represented by the general formula (1):

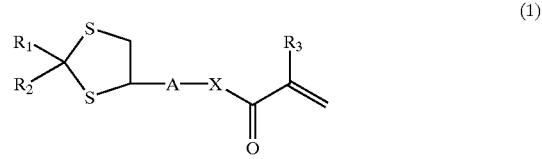

(1)

wherein, $R_1$ and $R_2$ represent independently a hydrogen atom, an alkyl group which may have a substituent, an aromatic alkyl group which may have a substituent or an aromatic residue which may have a substituent, respectively; $R_3$ represents a hydrogen atom or an alkyl group; A represents a divalent organic group; and X represents a sulfur atom or an oxygen atom; provided that when X is an oxygen atom, $R_1$ represents an aromatic residue that may have a substituent.

2. The acrylic ester compound according to claim 1, wherein in formula (1) $R_1$ represents an aromatic residue which may have a substituent, A represents $—(CH_2)_m—$ (m is an integer from 1 to 3), and X represents a sulfur atom.

3. A polymerizable composition comprising the acrylic ester compound according to claim 2.

4. A cured article obtained by polymerizing the polymerizable composition according to claim 3.

5. An optical component comprising the cured article according to claim 4.

6. A manufacturing method of the acrylic ester compound according to claim 2, wherein a sulfur-containing compound represented by the general formula (2) is esterified to form an acrylic ester:

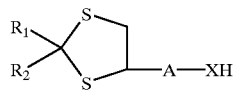
(2)

wherein, $R_1$ and $R_2$ represent independently a hydrogen atom, an alkyl group which may have a substituent, an aromatic alkyl group which may have a substituent or an aromatic residue which may have a substituent, respectively; A represents a divalent organic group; and X represents a sulfur atom or an oxygen atom; provided that when X is an oxygen atom, $R_1$ represents an aromatic residue that may have a substituent.

7. The manufacturing method according to claim 6, wherein in the general formula (2) $R_1$ represents an aromatic residue which may have a substituent, A represents —$(CH_2)_m$— (m is an integer from 1 to 3) and X represents a sulfur atom.

8. The manufacturing methods according to claim 7, wherein esterification to form an acrylic ester is performed by reacting the compound represented by the general formula (2) with halopropionic acids or acid halides thereof to form a halopropionic acid compound and then by dehalogenating the halopropionic acid compound.

9. A polymerizable composition comprising the acrylic ester compound according to claim 1.

10. A cured article obtained by polymerizing the polymerizable composition according to claim 9.

11. An optical component comprising the cured article according to claim 10.

12. A manufacturing method of the acrylic ester compound according to claim 1, wherein a sulfur-containing compound represented by the general formula (2) is esterified to from an acrylic ester:

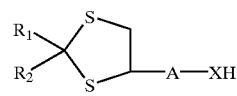
(2)

wherein, $R_1$ and $R_2$ represent independently a hydrogen atom, an alkyl group which may have a substituent, an aromatic alkyl group which may have a substituent or an aromatic residue which may have a substituent, respectively; A represents a divalent organic group; an X represent a sulfur atom or an oxygen atom; provided that when X is an oxygen atom, $R_1$ represents an aromatic residue that may have a substituent.

13. The manufacturing method according to claim 12, wherein in the general formula (2) $R_1$ represents an aromatic residue which may have a substituent, A represents —$(CH_2)_m$— (m is an integer from 1 to 3) and X represents a sulfur atom.

14. The manufacturing method according to claim 13, wherein esterification to form an acrylic ester is performed by reacting the compound represented by the general formula (2) with halopropionic acids or acids halides thereof to form a halopropionic acid compound and then by dehalogenating the halopropionic acid compound.

15. The manufacturing method according to claim 12, wherein esterification to form an acrylic ester is performed by reacting the compound represented by the general formula (2) with halopropionic acids or acids halides thereof to form a halopropionic acid compound and then by dehalogenating the halopropionic acid compound.

16. The manufacturing method according to claim 6, wherein esterification to form an acrylic ester is performed by reacting the compound represented by the general formula (2) with halopropionic acids or acids halides thereof to form a halopropionic acid compound and then by dehalogenating the halopropionic acid compound.

* * * * *